(12) United States Patent
Guillon et al.

(10) Patent No.: US 7,541,505 B2
(45) Date of Patent: Jun. 2, 2009

(54) PROCESS FOR THE PRODUCTION OF PHENYL ALKANES OPERATING IN A MOVING BED

(75) Inventors: Emmanuelle Guillon, Vernaison (FR); Eric Sanchez, Saint Genis Laval (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 400 days.

(21) Appl. No.: 11/448,680

(22) Filed: Jun. 8, 2006

(65) Prior Publication Data

US 2006/0287562 A1    Dec. 21, 2006

(30) Foreign Application Priority Data

Jun. 9, 2005    (FR) .................................. 05 05993

(51) Int. Cl.
   *C07C 2/66*    (2006.01)
(52) U.S. Cl. ..................... 585/455; 585/467; 585/901
(58) Field of Classification Search ................ 585/455, 585/467, 901
   See application file for complete search history.

(56) References Cited

U.S. PATENT DOCUMENTS

| 4,008,291 | A |  | 2/1977 | Zabransky et al. |
| 4,301,317 | A |  | 11/1981 | Young et al. |
| 4,973,780 | A |  | 11/1990 | Johnson et al. |
| 5,453,553 | A |  | 9/1995 | Sivansanker et al. |
| 5,675,048 | A |  | 10/1997 | Zhang et al. |
| 5,849,976 | A | * | 12/1998 | Gosling et al. ............. 585/709 |

FOREIGN PATENT DOCUMENTS

EP    0765849    4/1997

* cited by examiner

*Primary Examiner*—Thuan Dinh Dang
(74) *Attorney, Agent, or Firm*—Millen, White, Zelano & Branigan, P.C.

(57) ABSTRACT

A process for the production of phenyl alkanes by catalytic alkylation on a solid acid catalyst employs at least one moving-bed reactor. This process comprises a catalytic alkylation stage of an aromatic compound by at least one olefin that has 9 to 16 carbon atoms per molecule, combined with a catalyst reactivation circuit. Each reactor contains n reaction zones, whereby each of said zones consists of an acidic solid catalyst, optionally different from one zone to the next. Entering each reaction zone, a fraction of the total amount of olefins necessary to the alkylation reaction is introduced. The phenyl alkanes that are obtained by the process according to the invention are particularly suitable for the production of detergents.

20 Claims, 2 Drawing Sheets

PROCESS FOR THE PRODUCTION OF PHENYL ALKANES OPERATING IN A MOVING BED

TECHNICAL FIELD

This invention relates to a process for the production of phenyl alkanes by catalytic alkylation of an aromatic compound by means of olefinic hydrocarbons that in general comprise 9 to 16 atoms, and preferably 10 to 14 carbon atoms per molecule.

The phenyl alkanes that are obtained according to the process of the invention constitute precursors of choice for the formulation of detergents, and in particular certain biodegradable detergents, for example after sulfonation.

Currently, the bases for biodegradable detergents extensively employ alkyl benzenes or phenyl alkanes. The production of this type of compound is growing steadily. One of the primary properties sought for these compounds is their biodegradability that requires that said compounds be linear alkylbenzenes (LAB) or slightly branched alkyl benzenes (MAB) according to the definition of U.S. Pat. No. 6,187,981.

The alkylbenzenes are generally obtained by alkylation of the benzene by means of olefins that generally have 9 to 16 carbon atoms.

PRIOR ART

The best-known processes for alkylation of benzene use hydrofluoric acid as an acid catalyst. This process leads to the formation of 2-, 3-, 4-, 5- and 6-phenyl alkane isomers. The primary drawback of this process is linked to environmental constraints because it poses severe safety problems, on the one hand, and removal of waste problems, on the other hand.

In addition, the separation of the catalyst from the products of the reaction is difficult to implement. To solve these problems, a process for alkylation of benzene by linear olefins in the presence of an acidic solid catalyst was proposed.

The acidic solid catalysts constitute an advantageous alternative for the use of prior acid catalysts. The major drawback of the acidic solid catalysts, however, is their rapid deactivation during the alkylation reaction by adsorption at the surface of said catalysts of heavy hydrocarbon radicals, often designated overall as coke by one skilled in the art.

Several patents have already taught solutions for the purpose of limiting and even preventing the deactivation of acidic solid catalysts for alkylation.

For example, for a fixed-bed technology, U.S. Pat. No. 2,541,044 claims a continuous process for alkylation using several reactors operating in parallel with periodic alternation of each reactor from the alkylation reaction phase to a catalyst rejuvenation phase taking place at high temperature by means of an alkylated hydrocarbon flow.

In a similar manner, U.S. Pat. No. 5,648,579 discloses a continuous alkylation process in the presence of an acidic solid catalyst whose level of activity is maintained by alternately initiating an alkylation reaction stage (benzene+olefins) and a benzene washing stage, during which the olefin flow is interrupted for a cycle duration of 10 minutes to 1 hour.

U.S. Pat. No. 5,453,553 discloses a process for the production of linear alkyl benzenes in the presence of hydrogen with use of a solid catalyst that comprises a metal phase in close contact with a zeolite.

The prior processes disclosed in U.S. Pat. No. 5,648,579 and U.S. Pat. No. 5,453,553 require stopping the production of alkyl benzenes for the time that is necessary for the catalyst rejuvenation phase.

Several patents claim the use of continuous processes for the alkylation of aromatic compounds, i.e., processes in which the solid catalyst is in motion and circulates from an alkylation zone to a regeneration zone.

U.S. Pat. Nos. 5,675,048 and 5,789,640 claim an alkylation process that uses a fluidized-bed reactor in the liquid phase with a catalyst/hydrocarbon separation zone and one or more regeneration zones. The fluidized-bed technology is very different from that in a moving bed to the extent that it requires a separation of the catalyst and effluents from the reaction that does not exist in the moving-bed technology.

U.S. Pat. No. 4,973,780 claims a process for alkylation of benzene by olefins in a moving bed such that a portion of the deactivated catalyst is replaced periodically. The catalyst is regenerated by combustion of the coke in the presence of oxygen. Such a process leads to relatively low catalyst service lives taking into account the degradation of the physico-chemical properties of the catalyst subjected to numerous combustion cycles. Several patents claim the use of continuous processes for the alkylation of aromatic compounds, i.e., processes in which the solid catalyst is in motion and circulates from an alkylation zone to a regeneration zone.

U.S. Pat. Nos. 5,675,048 and 5,789,640 claim an alkylation process using a fluidized-bed reactor in the liquid phase with a catalyst/hydrocarbon separation zone and one or more regeneration zones. The fluidized-bed technology is very different from that of the moving bed to the extent that it requires a separation of the catalyst and effluents from the reaction that does not exist in the moving-bed technology.

U.S. Pat. No. 4,973,780 claims a process for alkylation of benzene by olefins in a moving bed such that a portion of the deactivated catalyst is replaced periodically.

The catalyst is regenerated by combustion of coke in the presence of oxygen. Such a process leads to relatively short catalyst service lives, taking into account the degradation of the physico-chemical properties of the catalyst subjected to numerous combustion cycles. In this invention, the regeneration cycle is coupled to the rejuvenation cycle, such that the regeneration is used with a more more limited frequency.

In addition, this patent is oriented to the production of ethyl benzene or cumene that requires operating conditions that are very different from those of this invention.

U.S. Pat. Nos. 4,008,291/4,028,430/4,049,739/4,072,729 and U.S. Pat. No. 5,523,503 claim the use of a process in simulated co- or countercurrent for the alkylation of aromatic compounds. In the processes in a simulated moving bed, the solid catalyst is immobile and the points for injection of the feedstock and draw-off of the effluents vary over time so that the behavior of such a reactor is equivalent to that with a circulation of catalytic solid. It is a technology that is more similar to fixed beds. Moreover, the management of variable injection and draw-off points over time is an important complication.

SUMMARY DESCRIPTION OF THE INVENTION

The process for continuous production of phenyl alkanes according to this invention employs at least one reactor that operates in a moving bed, whereby said reactor is divided into several reaction zones through which the feedstock and the effluents travel in succession, whereby each zone can operate with an identical or different catalyst, and whereby said catalyst is sent continuously into a rejuvenation circuit and sequentially into a regeneration circuit.

The novelty of this invention resides in the application of the moving-bed technology to the alkylation reaction of an aromatic compound, whereby the reactor that is used is divided into several reaction zones with staging of the feed into each of the reaction zones, and whereby each zone uses a rejuvenation circuit and a regeneration circuit, whereby said circuits in some cases can be common to several reaction zones.

In the moving-bed processes, the catalyst is generally in the form of approximately spherical particles, on the order of one millimeter in size, and it travels through the reactor in a downward flow at linear speeds on the order of one meter per hour.

Typically, the moving-bed processes of the catalytic reforming type employ one or more reactors that operate in series with a regeneration circuit of the catalyst that is common to all the reactors. The term series means that each reactor of the series is fed by the spent catalyst obtained from the preceding reactor.

The reactor according to the invention is divided into several reaction zones each comprising a catalyst that may be identical or different from one zone to the next.

In a general way, the catalyst of a given zone is drawn continuously leaving said zone to be introduced into the rejuvenation circuit, then after rejuvenation, it is reintroduced at the top of the zone from where it was drawn.

At certain time periods, the catalyst of the zone being considered is sent into the regeneration circuit, and then the regenerated catalyst is reintroduced at the top of the zone from where it was drawn.

In a preferred manner, the rejuvenation circuit will be common to the different reaction zones. Each reaction zone, however, optionally can have its own rejuvenation circuit. This is the case in particular for the reaction zones that have different catalysts. It is one skilled in the art who will choose the best configuration that is possible of the process in terms of decomposition of the reactor in several reaction zones, of the rejuvenation circuit and the regeneration circuit according to the economic constraints or the ease of operation.

The regeneration circuit can be common to several zones to the extent that the regeneration of the catalyst of several zones is not generally carried out simultaneously.

In the general configuration, the catalyst of one zone does not circulate in another zone. A configuration in which the same catalyst travels through a certain number of zones in succession, however, remains perfectly within the scope of the invention. In this case, the subset of the zones through which the same catalyst travels in succession has a rejuvenation circuit that is common to all of said zones, whereby the catalyst is drawn continuously leaving the last zone and then after rejuvenation is reintroduced at the top of the first zone of said series.

In the rest of the text, the term sub-series will be used to refer to the subset of the reaction zones through which the same catalyst travels in succession, where said subset of reaction zones exists.

This sub-series does not always exist, the reactor according to the invention being able to comprise only reaction zones without circulation from one zone to the next.

The process for the production of phenyl alkanes by alkylation of an aromatic compound according to the invention can therefore be defined in the most general manner as formed by a series of reaction zones in which it is possible to distinguish two subsets:

The subset of the reaction zones operating with a catalyst that does not circulate to another zone and that therefore have their own rejuvenation circuit. The catalyst of such a reaction zone is drawn leaving each of the zones, introduced continuously in the rejuvenation circuit and reintroduced after rejuvenation at the top of said zone.

The subset of the reaction zones through which the catalyst travels in succession. For this subset, the catalyst that is drawn leaving the last zone of the sub-series is introduced continuously into the rejuvenation circuit and reintroduced at the top of the first zone of said sub-series.

The feedstock of a reaction zone of row n consists of effluents of the reaction zone of row n−1, to which is added a fraction of the olefinic feedstock and optionally, when the latter is introduced in a fractionated manner, a fraction of the aromatic compound that is to be alkylated.

In a preferred manner, the aromatic compound that is to be alkylated is introduced in its entirety into the first reaction zone, but a fractionated introduction of said aromatic compound into each or a portion of the reaction zones remains perfectly within the scope of the invention.

The olefinic feedstock is always introduced in a fractionated manner into each of the reaction zones by respecting a certain ratio relative to the amount of total aromatic compound.

DETAILED DESCRIPTION OF THE INVENTION

This invention describes a process for the production of phenyl alkanes in a moving bed employing at least one reactor that is divided into several reaction zones, with staging of the introduction of the olefinic feedstock into each of the reaction zones and reactivation of the catalyst by means of a rejuvenation circuit operating continuously and a regeneration circuit that operates in a sequential manner.

In certain extreme cases, the regeneration could also be done continuously while remaining within the scope of the invention, but because of the existence of a rejuvenation circuit that operates continuously, the regeneration circuit will operate sequentially at an optimized frequency in the large majority of cases.

The careful controlling of the frequency of the regeneration makes it possible to very sensitively increase the service life of the catalyst and forms an integral part of the invention.

This invention also describes a process for the production of phenyl alkanes whose selectivity in linear or branched products, and, more generally, the concentration of 2-phenyl isomer, can be controlled by a suitable choice of the catalyst that is used in each reaction zone.

This invention therefore consists of a process for the production of phenyl alkanes by alkylation of an aromatic compound, by at least one olefin that has 9 to 16 carbon atoms per molecule and preferably that has 10 to 14 carbon atoms per molecule, whereby said reaction is implemented in at least one reactor that is divided into several reaction zones, each reaction zone operating in a moving bed with an acidic solid catalyst.

Preferably within the scope of the production of phenyl alkanes, the aromatic feedstock is introduced completely at the top of the first reaction zone, and the olefinic feedstock is introduced in the form of fractions in each of the reaction zones.

The olefins that are used as an alkylating agent in the catalytic reactor or reactors for alkylation according to the invention preferably contain 10 to 14 carbon atoms per molecule. Preferably, the olefins that are used for the alkylation reaction are for the most part linear, i.e., preferably the linear olefins represent at least 50% by weight of the olefinic feedstock that enters each reaction zone and preferably at least 60% by weight of said feedstock. In the case where the olefinic feedstock is obtained from an effluent of an n-paraffin dehydrogenation unit, the latter can contain up to 20% by weight of heavy aromatic compounds that are formed in the dehydrogenation unit, in addition to the unconverted linear paraffins and olefins.

The aromatic compound that is used as a reagent in the catalytic reactor or reactors for alkylation is preferably benzene.

The different reaction zones operate in series from the feedstock/effluent standpoint in that the feed of the reaction zone n consists of the olefinic feedstock fraction for alkylation, effluents of the reaction zone n–1, and optionally an aromatic compound fraction that is to be alkylated.

In a general manner, the catalyst of each reaction zone is drawn leaving said zone, directed continuously to a rejuvenation zone, then is reintroduced at the top of said reaction zone.

The same catalyst travels in succession through certain reaction zones that form a sub-series, whereby said catalyst is then drawn leaving the last zone of the sub-series, introduced into the rejuvenation circuit that is common to the zones of said sub-series, and reintroduced after rejuvenation at the top of the first reaction zone of said sub-series.

According to an embodiment of the invention, the catalyst of each reaction zone is sequentially drawn leaving said zone, introduced into the regeneration circuit, then generally passes into the rejuvenation circuit and is reintroduced at the top of the reaction zone that is considered.

The rejuvenation circuit is characterized by washing the catalyst by means of an aromatic hydrocarbon flow, generally benzene.

The regeneration circuit is characterized by a controlled combustion of the hydrocarbon compounds that are adsorbed on the surface of the catalyst.

In the text below, in a general way, reactivation is mentioned to designate one or the other of the rejuvenation or regeneration circuits.

More specifically, the rejuvenation consists in washing the partially deactivated solid catalyst by an aromatic compound that is brought to a temperature of generally more than 100° C.

Advantageously, said aromatic compound is benzene.

The rejuvenation is carried out after having transported the catalyst by means of a transport hose called a "liquid lift" to a tank called a rejuvenation tank, in which the acidic solid catalyst is brought into contact with the aromatic compound that allows the washing of the catalyst at a temperature that is usually more than the temperature of the alkylation. The temperature at which the rejuvenation is carried out is generally more than 100° C., preferably more than 150° C., and even more preferably more than 200° C. The rejuvenation is carried out for an adequate period, advantageously on the order of several hours so as to guarantee the complete elimination of hydrocarbons that are adsorbed on the active sites of the solid catalyst.

The regeneration typically comprises a phase of managed combustion of the carbon deposits formed on the catalyst, for example with an air/nitrogen mixture, or air that is low in oxygen or simply air, preferably dehydrated, and can optionally comprise other additional phases for treating catalyst.

The regeneration zone can also be operated in a moving bed or in a fixed bed at a pressure that is generally close to the mean pressure of the process and at a temperature that is generally between 400° C. to 650° C.

The regeneration zone optionally can be operated at a lower pressure in this case by means of a buffer tank between the separator and the regenerator.

Having undergone a reactivation by rejuvenation and/or by regeneration, the catalyst is then transferred by lift or by flow of gravity based on the geometry of the installation to the input of the reaction zone in which it works or entering the series of reaction zones if several reaction zones are affected by the same catalyst.

As a whole, the catalyst can circulate in co-current relative to the feedstock or in cross-current. In the latter case, the feedstock is introduced at the periphery of the reaction zone being considered, then it is collected in a central well that is located approximately at the center of said reaction zone. To obtain other details on the processes in the moving bed, it will be possible to refer in particular to U.S. Pat. Nos. 3,838,039, 5,336,829, 5,849,976 and to Patent Application EP 1 195 424A1. A reverse circulation of the feedstock from the center of the reactor to the periphery is also possible.

Because of the continuous reactivation of the catalyst, the catalytic performances are maintained at peak levels for very long operational periods, and there is no longer any notion of cycle length as in the processes that are obtained from the prior art.

In addition, the process according to the invention also has the advantage of producing phenyl alkanes whose selectivity of linear products, i.e., that do not exhibit branches on the alkyl chain carried by the benzene group, and particularly the 2-phenyl selectivity, can be controlled, which is advantageous because the specifications of the products desired for an application in the formulation of detergents are "very variable."

Another advantage of the invention is the optimization of the amount of olefinic feedstock to be introduced into the different reaction zones of the catalytic reactor or reactors. Actually, contrary to the prior processes in which the entire amount of olefins is generally introduced at one time, the process according to the invention makes it possible, by the fractionation of the olefinic feedstock, to reduce the amount of benzene necessary relative to the prior processes, while keeping the same aromatic compound(s)/olefins ratio, preferably benzene/olefins ratio, in the catalytic reactor or reactors.

This possibility of modulating the aromatic compound/olefins ratio represents a savings on the level of the initial investment, the operating cost, and makes it possible, in combination with the continuous rejuvenation of the catalyst, to considerably increase the service life of said catalyst.

In addition, contrary to certain prior processes, the process according to the invention does not require the elimination, upstream from the alkylation reactor or reactors, of the coke precursor compounds that are responsible for the deactivation, i.e., essentially the heavy aromatic compounds that are obtained from, for example, a dehydrogenation unit.

Actually, the continuous rejuvenation of the catalyst makes it possible to tolerate these heavy aromatic compounds in the alkylation feedstock up to contents of 80% in the olefinic feedstock, whereby said percentage is related to the single olefinic and aromatic compounds (i.e., by excluding the other compounds that are present in the alkylation feedstock, such as the normal paraffins).

It is quite clear for one skilled in the art that the frequency of the regeneration will be primarily conditional on the content of these aromatic compounds, precursors of the deactivation, in the alkylation feedstock.

The rest of the description will be better understood by following FIGS. 1 and 2 in which are shown respectively the circuit of the feedstock and effluents, the circuit of the catalyst for the rejuvenation circuit (FIG. 1), and the circuit of the catalyst for the regeneration circuit (FIG. 2) with a reaction zone number n that is equal to 2.

Figure 1:
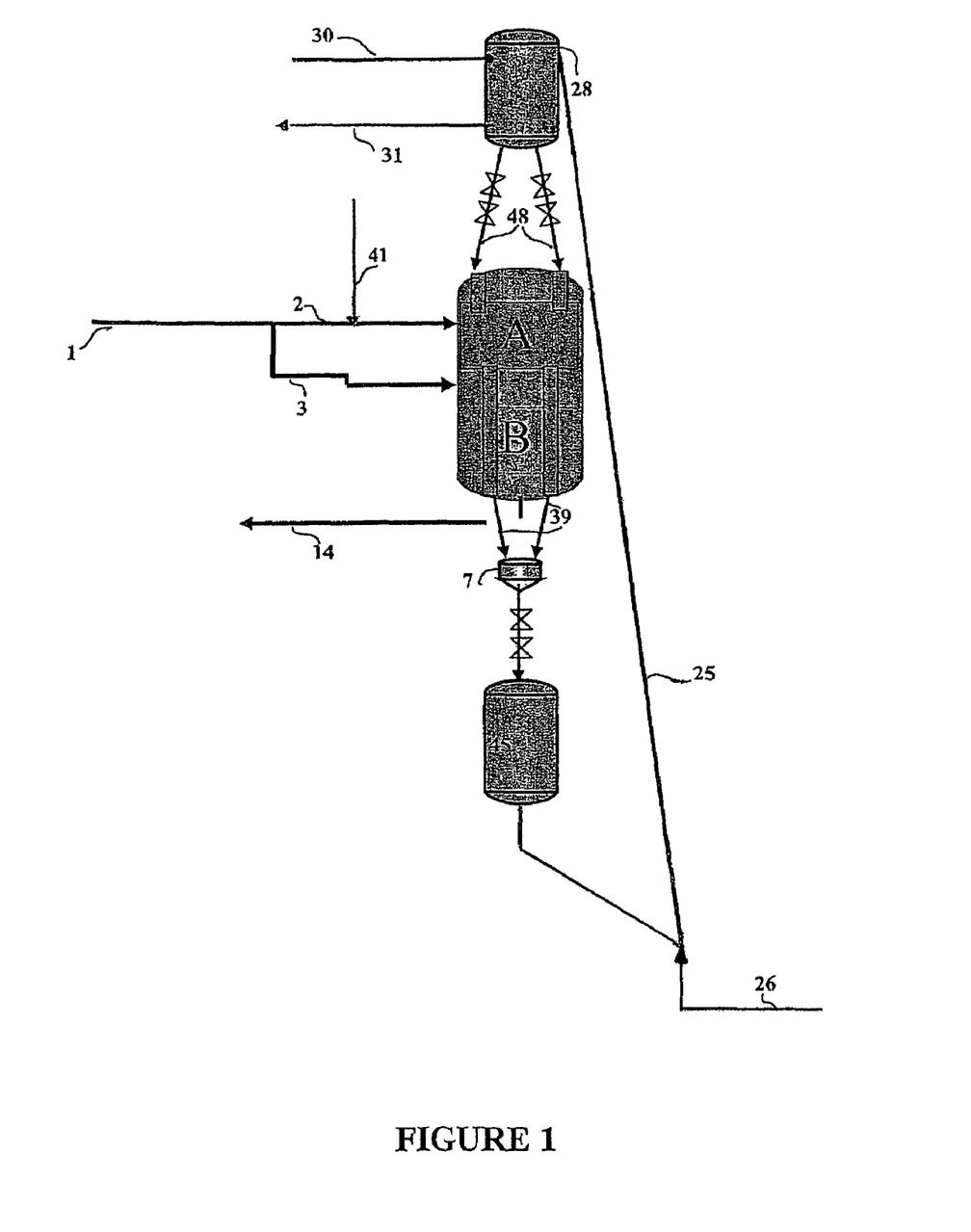
Figure 2:
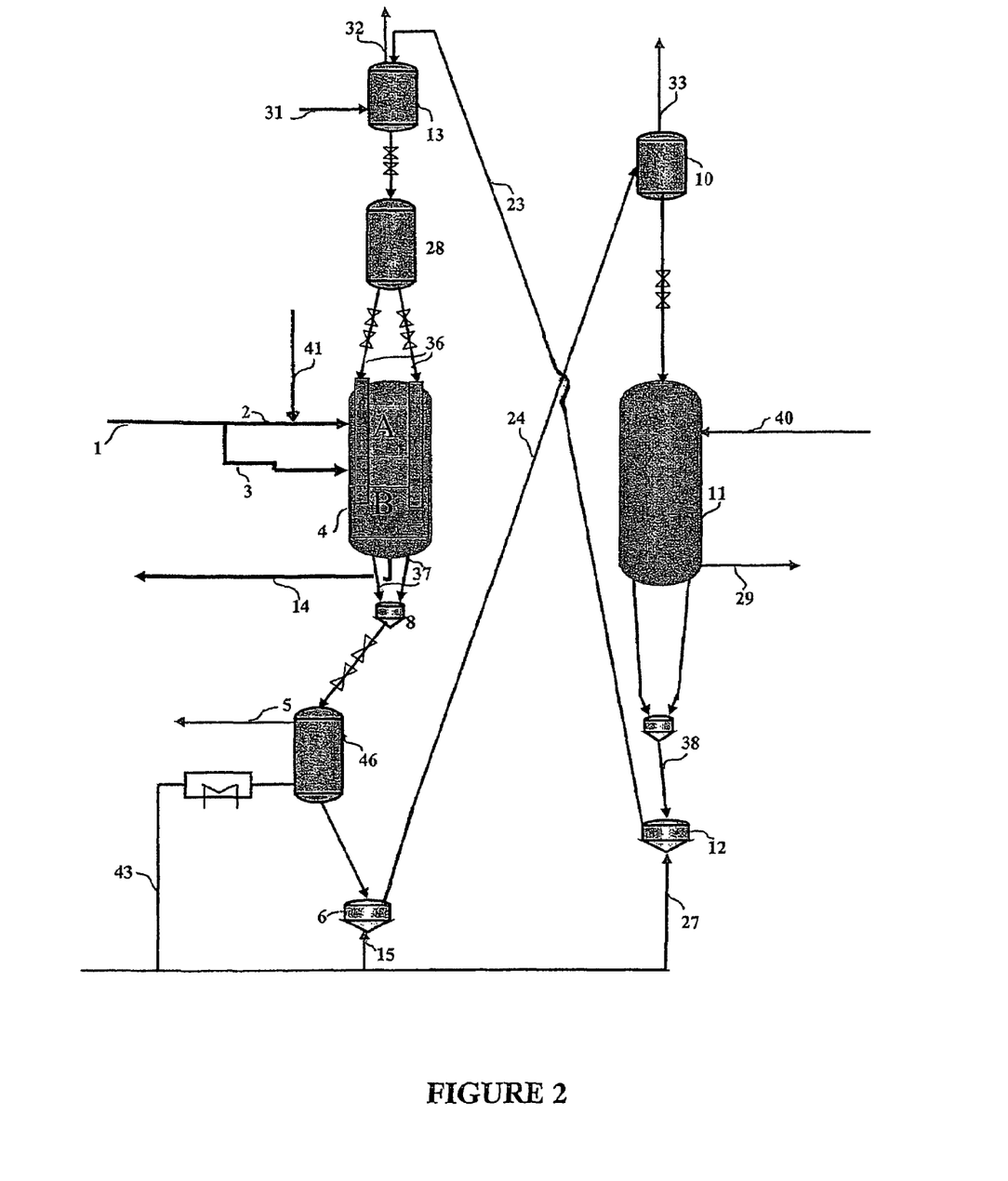

In these figures, two reaction zones, denoted A and B, without circulation of catalyst from one to the other, are shown.

The decomposition in two figures is done only for the clarity of understanding, but the process according to the invention duly comprises a continuous rejuvenation circuit and a sequential regeneration circuit.

The installation that makes it possible to carry out the process for the production of phenyl alkanes according to the invention therefore comprises at least one catalytic reactor for alkylation (4), a rejuvenation tank (28), and a regeneration tank (11), called regenerator (11) below. The reactor (4) is divided into two reaction zones, an upper reaction zone (A) and a lower reaction zone (B), each equipped with means for introduction of the catalyst (48) and for draw-off (39) for the reaction zone (A) that is located in the upper portion of the reactor (FIG. 1) and means for introduction (36) and for draw-off (37) of the catalyst for the reaction zone (B) that is located in the lower portion of the reactor (4) (FIG. 2). The draw-off means also comprise at least one reservoir (45) that is fed from an intermediate pot (7) that makes it possible to direct the catalyst to the rejuvenation circuit and a reservoir (46) that is fed from an intermediate pot (8) that makes it possible to direct the catalyst to the regeneration circuit. The intermediate pots (7) and (8) can optionally be combined.

The olefinic feedstock (1) is divided into a fraction (2) that feeds the reaction zone A and a fraction (3) that feeds the reaction zone B.

The olefinic feedstock fraction (2) is mixed with the aromatic compound that is introduced integrally via the line (41) to constitute the feedstock of the reaction zone A.

The olefinic feedstock fraction (3) is mixed with the effluents of the reaction zone A (not shown in the figures) to constitute the feedstock of the reaction zone B.

The reaction effluents of the reaction zone B are evacuated from said zone via the line (14) where they are directed to a fractionation zone that is not shown in FIGS. 1 and 2.

The number n of reaction zones of each reactor is between 1 and 10, and preferably between 1 and 5.

Entering each of the reaction zones, a fraction of the total amount of olefins that is necessary to the alkylation reaction of the aromatic compound, preferably benzene, is introduced so that the ratio of the weight of the aromatic compound to be alkylated to the weight of olefins entering each reaction zone is between 30 and 100, and preferably between 30 and 70.

It is also very advantageous for a catalytic reactor that comprises n reaction zones that the olefin fraction introduced into each of the reaction zones represents essentially 1/n of the total amount of olefins necessary to the alkylation reaction.

According to another method of operation, the olefin fraction that is introduced entering each of the reaction zones is such that the ratio by weight of the aromatic compound to be alkylated to the olefins is staged in the upward or downward direction in each of said reaction zones. That is to say that this ratio can be increased (or reduced) according to a certain progression, when a passage from the reaction zone of row n to the reaction zone of row n+1 is made for reasons of product quality or stability of the catalyst.

The ratio that is mentioned above can also be modified by adjusting the fraction of the aromatic compound that is to be alkylated when the latter is introduced in a fractionated manner.

Each olefinic feedstock fraction is generally contained in a hydrocarbon feedstock that primarily contains paraffins. The paraffins that are contained in said feedstock are $C_9$-$C_{16}$ paraffins, preferably $C_{10}$-$C_{14}$ paraffins. The olefins generally represent from 5 to 100% by weight of the hydrocarbon feedstock that is introduced entering each of the reaction zones.

Each of the reaction zones is operated at a temperature of less than 400° C., generally between 50° C. and 350° C., preferably between 70° C. and 300° C., and even more preferably between 80° C. and 250° C.

Each reaction zone operates under a pressure of 1 to 10 MPa (megapascal, 1 MPa=10 bar), preferably under a pressure of 1 to 7 MPa, with a liquid hydrocarbon flow rate whose volumetric flow rate is from about 0.1 to 80, and preferably from 0.5 to 50 volumes per volume of catalyst and per hour.

The alkylation reaction that is used in the catalytic reactor or reactors for alkylation according to the invention is generally followed by at least one separation stage so as to recover the excess reagents, on the one hand, and the desired phenyl alkanes, on the other hand.

More specifically, leaving the catalytic reactor for alkylation, in general the effluents of said reactor that are evacuated via the line (14) are fractionated so as to collect separately a) a first effluent containing the aromatic compound, preferably benzene, unconverted, b) a second effluent containing at least one linear olefin $C_9$-$C_{16}$, preferably $C_{10}$-$C_{14}$, unconverted, as well as the paraffins and optionally the aromatic compounds, c) a third effluent containing the 2-, 3-, 4-, 5- and 6-phenyl alkanes, and d) a fourth effluent that contains at least one poly-alkylbenzene (or polyalkyl benzene fraction), the latter optionally able to be, at least partially, recycled to one of the reaction zones, where it reacts with the aromatic compound, preferably benzene, upon contact with the acidic solid catalyst contained in said reaction zone, so as to be at least partly transalkylated (according to a transalkylation reaction), and a mixture of 2-, 3-, 4-, 5- and 6-phenyl alkanes is collected.

Description of the Rejuvenation Circuit (FIG. 1)

The rejuvenation consists in transferring the catalyst drawn leaving a reaction zone (zone A in the case of FIG. 1) to the reservoir (45) by means of legs (39).

From the reservoir (45), the catalyst is transported by a liquid lift (25) that is fed by a liquid flow (26) (a gaseous lift also being possible by means in this case of a draining of the tank (45)), to a rejuvenation tank (28) that is located, for example, above the alkylation reactor (4), then in washing said at least partially deactivated catalyst by an aromatic compound that is introduced via the line (30).

The washing effluents containing the aromatic washing compound and the hydrocarbons that are adsorbed on the surface of the catalyst are evacuated from the rejuvenation tank (28) via the line (31). The rejuvenated catalyst is reintroduced at the top of the reaction zone A by means of the legs (48).

Advantageously, said aromatic compound is benzene. The rejuvenation is carried out in the absence of olefinic hydrocarbons since, generally, the catalyst before transport undergoes a stage for separation of the effluents from the reaction at the level of the tank (45).

The temperature at which the rejuvenation is carried out is generally more than 100° C., preferably more than 150° C., and even more preferably more than 200° C.

The rejuvenation is carried out for an adequate period so as to guarantee the complete elimination of adsorbed hydrocarbons in the active sites of each of the acidic solid catalysts. This duration depends on the deactivation level of the catalyst but also on the hydrodynamic conditions used in the rejuvenation tank (28) during washing, in particular the linear speed of the washing agent that generally will be more than 1 m/s.

The catalyst that is continuously drawn off from the rejuvenation tank (28) by means of the downward legs (48) is sent, generally by gravity, to the reaction zone from which it was drawn (zone A in FIG. 1).

In the case of a catalyst that is drawn leaving a reaction zone belonging to a sub-series (as this term is defined in the summary description paragraph of the invention), the rejuvenated catalyst is reintroduced at the top of the first reaction zone of said sub-series.

Description of the Regeneration Circuit (FIG. 2)

The regeneration consists in transferring the catalyst from the reaction zone (denoted B in FIG. 2) to a tank (46) via legs (37) and intermediate pot (8), then in transferring the catalyst from tank (46) to lifting pot (6) from which it is transported by means of the transport gas (15) to a separator tank (10) from which it is transferred by gravity to the regenerator (11).

The separator tank (10) makes possible the separation of the catalyst and the transport gas and the elimination of optional fine particles formed by attrition during said transport. Inside the regenerator (11), the catalyst undergoes a controlled combustion of the hydrocarbon radicals adsorbed on its surface by means of a combustion gas that is introduced via the line (40). The combustion effluents are evacuated via the line (29) to a specific regeneration circuit that is known by one skilled in the art.

The regenerated catalyst is transferred into an intermediate pot (38), then from the intermediate pot (38), it is picked up in the transport pot (12), fed by the transport gas (27) to be brought into a separator tank (13) inside of which the catalyst is separated from the transport gas and fine particles optionally formed during said transport.

The regenerated catalyst leaving the separator tank (13) is preferably reintroduced into the rejuvenation tank (28) before being brought via legs (36) into the reaction zone B.

A configuration in which the regenerated catalyst would be directly reintroduced into the reaction zone B from the separator tank (13) would nevertheless remain within the scope of the invention.

The reaction zone in which the regenerated catalyst is reintroduced can be either the reaction zone from which it had been drawn or the first reaction zone of a sub-series of reaction zones using the same catalyst in the meaning defined in the summary description paragraph of the invention.

The regeneration is carried out by combustion of the hydrocarbon radicals adsorbed on the active sites of the catalyst.

More specifically, the regeneration of the catalyst by combustion comprises:

Optionally a first stage that is generally carried out in a tank (46) before the transport of the catalyst to the regenerator, consisting in heating under cover gas (43), to a temperature of more than 100° C. and preferably between 150° C. and 250° C., and even more preferably between 200° C. and 300° C., said deactivated catalyst, so as to eliminate the liquid hydrocarbons that are adsorbed by the line (5), and A second stage consisting in bringing into contact the catalyst with a gas that contains oxygen (40) in the regeneration tank (11) by gradually increasing the temperature until the exothermal coke combustion reaction is observed, in general between 300° C. and 600° C., and preferably between 400° C. and 500° C.

The first heating stage under cover gas makes it possible to prevent any risk of an uncontrolled temperature increase during the second stage, which corresponds to the actual coke combustion itself.

The majority of the coke is burned during the combustion stage.

The content by weight of residual coke on the catalyst after combustion is generally less than 20% and preferably less than 10% of the coke content on the catalyst before said combustion.

The gas that contains the oxygen used during the combustion stage is generally a mixture of oxygen and cover gas, advantageously containing 0.1% to 20% by volume of oxygen and preferably 0.2% to 10% by volume of oxygen.

It can be, for example, air or air diluted in a cover gas.

The regeneration is triggered at time periods determined from indicators that are generally placed in a line and that directly or indirectly reflect the degree of deactivation of the catalyst.

Among the indicators that are well known to one skilled in the art, it is possible to cite the conversion of olefins introduced into each reaction zone, the level of coke deposited on the catalyst, or else the operating temperature in the reaction zones, or else and preferably, the temperature difference between the output and the input of each reaction zone that generally will be kept at a certain value.

More specifically, in a preferred configuration, the reactor for the production of phenyl alkanes by alkylation of an aromatic compound by an olefinic feedstock according to the invention consists of a series of n reaction zones, whereby each reaction zone has at least one thermocouple for measuring the temperature at the input and the output of said zone, and the regeneration sequence of the catalyst that is contained in said zone is triggered when the temperature difference between the output and the input of said zone exceeds a certain value.

The catalysts that are used in the process according to the invention are all acidic solid types that can carry out the alkylation reaction. They can be amorphous or crystallized acidic solids.

Among the amorphous catalysts, the alumina silicas, aluminas that may or may not be doped by halogens, are preferred.

Among the crystallized catalysts, the crystalline-structure zeolites, for example having a structure as defined in the classification "Atlas of Zeolite Framework Type" (atlas of different geolite structure types), (W. M. Meier, D. H. Olson and Ch. Baerlocher, 5$^{th}$ Revised Edition, 2001, Elsevier), are preferred.

The catalyst preferably comprises at least one zeolite that is selected from the group that consists of the zeolites of the FAU, MOR, MTW, OFF, MAZ, BEA EUO, UTL and NES structural type.

In a preferred manner, the catalyst that is contained in each, or at least a portion of the reaction zones, comprises at least one Y zeolite, advantageously a dealuminified Y zeolite, with an overall Si/Al atomic ratio of more than 4, preferably of between 8 and 100, and even more preferably between 15 and 70.

According to another embodiment of this invention, it may be advantageous to use a mixture of catalysts as an acidic solid catalyst in each of the reaction zones. It may be, for example, a mixture of a crystallized catalyst and an amorphous catalyst. It also may be a mixture of zeolites that consists of at least one Y zeolite as described above and at least one MOR-structural-type zeolite, in particular a mordenite zeolite.

The process for the production of phenyl alkanes by alkylation of an aromatic compound according to the invention can contain, in some of the reaction zones, a crystallized acidic solid catalyst of the structural type that is selected from the group that is formed by FAU, MOR, MTW, OFF, MAZ, BEA EUO, UTL and NES.

The catalyst that is used in at least a portion of the reaction zones can also be an amorphous solid catalyst that is selected from the group that is formed by the alumina silicas and the aluminas that may or may not be doped by halogenated compounds.

In some of the reaction zones, the process for the production of phenyl alkanes by alkylation of an aromatic compound according to the invention can contain a mixture of at least two crystallized solid catalysts of a structural type that is selected from the group that is formed by FAU, MOR, MTW, OFF, MAZ, BEA EUO, UTL and NES.

Finally, in some cases, the process for production of phenyl alkanes according to the invention can contain in certain reaction zones a mixture of at least one crystallized solid catalyst of a structural type that is selected from the group that is formed by FAU, MOR, MTW, OFF, MAZ, BEA EUO, UTL, and NES and an amorphous solid catalyst that is selected from the group that is formed by the alumina silicas and the aluminas that may or may not be doped by halogenated compounds.

The mixing of said zeolites, being found in the powder state, can be carried out by all powder-mixing techniques known to one skilled in the art and can be followed by shaping.

In particular, the mixing can be carried out with a generally amorphous matrix or with a moist powder of alumina gel. The shaping can also be carried out with matrices other than alumina, such as, for example, magnesia, amorphous silica-aluminas, natural clays (kaolin, bentonite, sepiolite, attapulgite), silica, titanium oxide, boron oxide, zirconia, aluminum phosphates, titanium phosphates, zirconium phosphates, carbon and mixtures thereof.

It is generally preferred to use matrices that contain alumina, under all the forms that are known to one skilled in the art, and even more preferably containing gamma-alumina.

The catalyst that is contained in each of the reaction zones of the catalytic reactor or reactors for alkylation for the implementation of the process according to the invention is shaped into grains of a shape and size compatible with the various transport modes used in this invention.

The catalyst that has to circulate inside the reaction zones in a moving bed is most often in the form of spherical balls with a ball diameter of several millimeters, typically 0.5 to 5 mm, and preferably 1 to 4 mm.

For the production of the catalyst, it is possible to use standard techniques, for example to mix the zeolite with precursors of silica gel and/or silica gels, then to shape small balls by coagulation of drops, to dry then to calcine said balls to obtain the final catalyst with the suitable shape and size.

After the shaping stage, the solid that is obtained is subjected to a drying stage at a temperature of between 100 and 300° C., preferably between 120 and 200° C., then to a calcination stage at a temperature of between 300 and 600° C., preferably between 350 and 550° C.

EXAMPLE ACCORDING TO THE INVENTION

The invention will be better understood from reading the following detailed example that is representative of a particular embodiment of a reactor according to the invention.

This example is by no means limiting and is only intended to illustrate a particular embodiment of the process according to the invention.

The alkylation reactor that is used comprises 2 reaction zones, an upper reaction zone denoted A and a lower reaction zone denoted B. There is no circulation of catalyst from one zone to the next.

The catalyst that is used in the two zones consists of 70% by weight of dealuminified Y zeolite with an Si/Al ratio of 30.

The size of the spherical catalyst particles is 2.5 mm.

The olefinic alkylation feedstock (1) has the following composition:
C9 to C16 paraffins: 85% by weight
C9 to C16 olefins: 10% by weight
C9 to C16 aromatic compounds: 5% by weight The olefinic feedstock for alkylation (1) is divided into a first fraction (2) that is introduced into the first reaction zone (A) and a second fraction (3) that is introduced into the second reaction zone (B).

The feedstock that consists of benzene (41) is mixed with the alkylation feedstock (1) and then introduced into the reaction zone (A) via hose (2). The ratio by weight of benzene/olefin is equal to 60. All of the benzene is introduced at the top of the reactor.

The feeding of the reaction zone (B) consists of the reaction effluent of the reaction zone (A) and the olefinic feedstock flow (3).

Leaving the second reaction zone (B), the reaction effluent is sent via hose 14 to a separation section that is not shown in FIG. 1.

The reaction zones A and B operate at a temperature of 120° C. under a pressure of 4 MPa.

The separation section, not shown, comprises several fractionation columns and has as its object to separate the desired reaction products, i.e., primarily a mixture of 2-phenyl alkane, 3-phenyl alkane, 4-phenyl alkane, 5-phenyl alkane and 6-phenyl alkane that is sent into storage.

The catalyst of reaction zones A and B is drawn off respectively by the downward legs (39) and (37). So as to illustrate the typical operation of the installation, the rejuvenation circuit (see FIG. 1) will be described for the catalyst that is obtained from the reaction zone (A), and the regeneration circuit (see FIG. 2) will be described for the catalyst that is obtained from the reaction zone (B). It is necessary, however, to recall that the preferred mode of operation of this invention consists in continuously rejuvenating the catalyst that is obtained from the reaction zones A and B in the same rejuvenation circuit (the catalysts of zones A and B being identical and drawn off in parallel) and in regenerating sequentially the catalyst that is obtained from the reaction zones A and B in the same regeneration circuit. The rejuvenation and the regeneration coexist in operation, each with their specific circuit.

Rejuvenation Circuit (FIG. 1)

The catalyst that is obtained from the reaction zone (A) is drawn off by the downward leg (39) and sent into an intermediate pot (7) then into the tank (45) before being transferred via a liquid lift (25) to the rejuvenation tank (28) that is fed by benzene at 250° C. via the line (30).

The washing effluent that contains the washing benzene and the products that are adsorbed at the surface of the catalyst are evacuated via the line (31) and are sent to the separation section. The transport liquid that feeds the liquid lift (25) is introduced via the line (26).

The rejuvenated catalyst is reintroduced at the top of the reaction zone (A) via downward legs (48).

The rejuvenated catalyst is brought into contact in the reaction zone (A) with the benzene to be alkylated (41) and the olefinic feedstock (2).

Regeneration Circuit (FIG. 2)

The catalyst that is obtained from the reaction zone (B) is drawn off via the downward leg (37) and sent into an intermediate pot (8) then into the tank (46) inside of which it undergoes a draining, a preheating and a stripping up to a temperature of 300° C. by means of hot nitrogen that is introduced via the line (43).

The catalyst is then transferred into a lifting pot (6) so as to be conveyed via a gaseous lift (24) fed by the transport nitrogen (15) to the upper hopper (10) that is located above the regeneration tank (11).

By flow of gravity, the catalyst is then conducted to the regenerator (11) where it undergoes a managed combustion in the presence of air that is introduced via the line (40).

The combustion gases are evacuated from the regenerator (11) via the line (29) and are sent to a specific regeneration circuit (not shown in FIG. 2).

Leaving regenerator (11), the regenerated catalyst passes into a hopper (38) then into a lifting pot (12) so as to be conveyed into the upper hopper (13) via a pneumatic transport system (23) that operates with nitrogen (27).

In the upper hopper of the reactor (13), the catalyst undergoes flushing by a gas (31) that makes it possible to evacuate the fines that optionally are created during the transport that are directed via the line (32) to a particle filter, not shown.

The catalyst is transferred into the rejuvenation tank (28) where it is brought into contact with benzene before being reintroduced into the reaction zone (B) of the reactor (4) by means of downward legs (36). In the reaction zone B, the regenerated catalyst is brought into contact with the reaction feedstock that results from the olefinic feedstock (3) and effluents of the reaction zone (A).

The catalyst flows by gravity into the reaction zone (B) and is collected at the bottom in a hopper (46) via the pot (8).

The characteristics of the LAB (abbreviation of linear alkyl benzene according to English terminology) products are as follows:

2 Phenyl alkanes: more than 25% by weight
Tetralins: less than 0.5% by weight
Density: 0.86 kg/l
Degree of linearity: More than 92%

The invention claimed is:

1. A process for the production of phenyl alkanes comprising conducting alkylation of an aromatic compound with a feedstock that contains C9 to C16 olefins, providing at least one reactor divided into several reaction zones having a top and a bottom, each reaction zone containing a moving bed of an acidic solid catalyst, passing the catalyst from each reaction zone continuously into a rejuvenation circuit, reintroducing resultant rejuvenated catalyst into the top of said reaction zone, and wherein the catalyst of each reaction zone is periodically sequentially sent into a regeneration circuit leaving said reaction zone, then is reintroduced at the top of said reaction zone.

2. A process for the production of phenyl alkanes by alkylation of an aromatic compound by a feedstock that contains C9 to C16 olefins according to claim 1, in which a portion of the reaction zones forming a sub-series operate with the same catalyst that travels through them successively in a moving bed, whereby said catalyst leaving the last zone of the sub-series, is introduced continuously in the rejuvenation circuit then after rejuvenation is reintroduced at the top of the first zone of said sub-series, wherein said catalyst leaving the last zone of the sub series is sent sequentially into the regeneration circuit and, after regeneration, is reintroduced at the top of the first zone of said sub-series.

3. A process for the production of phenyl alkanes by alkylation according to claim 1, in which the olefinic feedstock for alkylation contains olefins that range from C10 to C14, and the aromatic compound that is to be alkylated is benzene.

4. A process for the production of phenyl alkanes by alkylation according to claim 1, in which only a fraction of stoichiometrically required olefin feedstock is introduced in each reaction zone so that the aromatic compound/olefin weight ratio at the input of each reaction zone is between 30 and 100.

5. A process for the production of phenyl alkanes by alkylation of an aromatic compound according to claim 1, in which the catalyst in at least one reaction is zone comprises a crystallized acidic solid catalyst selected from the group consisting of FAU, MOR, MTW, OFF, MAZ, BEA EUO, UTL and NES, and mixtures thereof.

6. A process for the production of phenyl alkanes by alkylation of an aromatic compound according to claim 1 in which the catalyst in at least one reaction zone comprises an amorphous solid catalyst selected from the group consisting of alumina silicas, aluminas doped with halogenated compounds, and aluminas undoped with halogenated compounds and mixtures thereof.

7. A process for the production of phenyl alkanes by alkylation of an aromatic compound according to claim 1, in which the catalyst at least one reaction zone comprises a dealuminified Y zeolite of the Si/Al ratio of between 8 and 100.

8. A process for the production of phenyl alkanes by alkylation of an aromatic compound according to claim 1, in which the size of the catalyst grains in each of the reaction zones is between 0.5 and 5 mm.

9. A process for the production of phenyl alkanes by alkylation of an aromatic compound according to claim 1, in which the catalyst in at least one reaction zone comprises a mixture of at least two crystallized solid catalysts selected from the group consisting of FAU, MOR, MTW, OFF, MAZ, BEA EUO, UTL and NES.

10. A process for the production of phenyl alkanes by alkylation of an aromatic compound according to claim 1, in which the catalyst in at least one reaction zone comprises a mixture of zeolites, wherein one of the components of the mixture is a dealuminified Y zeolite with an Si/Al ratio of between 8 and 100, and the other zeolite of the mixture is an MOR structural-type zeolite.

11. A process for the production of phenyl alkanes by alkylation of an aromatic compound according to claim 1, in which the catalyst in at least one reaction zone comprises a mixture of (A) at least one crystallized solid catalyst selected from the group consisting of FAU, MOR, MTW, OFF, MAZ, BEA EUO, UTL, and NES, and (B) at least one amorphous solid catalyst that is selected from the group consisting of the alumina silicas, aluminas doped by halogenated compounds, and aluminas undoped with halogenated compounds.

12. A process for the production of phenyl alkanes by alkylation of an aromatic compound according to claim 1, wherein said feedstock contains a content of heavy aromatic compounds up to 80% by weight, relating to the total weight of olefins and aromatic compounds.

13. A process for the production of phenyl alkanes by alkylation of an aromatic compound according to claim 1, in which the alkylation temperature is between 50° C. and 350° C., and the pressure is between 1 and 10 MPa.

14. A process for the production of phenyl alkanes by alkylation of an aromatic compound according to claim 1, wherein the regeneration of the catalyst is conducted with a combustion gas which contains 0.1 to 20% by volume of oxygen, and the combustion temperature is between 300° C. and 600° C.

15. A process for the production of phenyl alkanes by alkylation of an aromatic compound according to claim 1, wherein said rejuvenation circuit comprises as a rejuvenating agent an aromatic compound and the temperature of the rejuvenation is more than 100° C.

16. A process according to claim 2, comprising providing a reactor for the production of phenyl alkanes by alkylation of an aromatic compound by an olefinic feedstock comprising a series of n reaction zones, and conducting the reaction in A first subset of reaction zones through which the catalyst that circulates in a moving bed travels in succession, whereby the catalyst that is drawn leaving the last zone of the first subset is introduced continuously in the rejuvenation circuit and reintroduced at the top of the first zone of said first subset, and whereby said catalyst is sequentially sent into the regeneration circuit A second subset that comprises reaction zones that operate with a catalyst that operates in a moving bed, whereby each reaction zone has a suitable rejuvenation circuit, whereby the catalyst is drawn leaving each of the zones, introduced continuously into the rejuvenation circuit, and reintroduced after rejuvenation at the top of the zone from where it was drawn, and whereby said catalyst is sequentially sent into the regeneration circuit, whereby the feedstock of a reaction zone of row n comprises effluents of the reaction zone of row n−1, to which are added a fraction of the olefinic feedstock, and whereby the aromatic compound that is to be alkylated is introduced at the input of the first reaction zone.

17. A process according to claim 16 wherein the reactor comprises a series of n reaction zones, whereby n is between 1 and 10.

18. A process according to claim 4, wherein said weight ratio of aromatic compound/olefin is between 30 and 70.

19. A process according to claim 2, wherein the aromatic compound is benzene.

20. A process according to claim 19, wherein the aromatic compound is benzene.

\* \* \* \* \*